United States Patent
Mills

(10) Patent No.: US 7,762,255 B2
(45) Date of Patent: Jul. 27, 2010

(54) SAFETY DEVICE FOR BREATHING CIRCUIT CARBON DIOXIDE ABSORBER

(75) Inventor: Julie Anne Mills, Monona, WI (US)

(73) Assignee: General Electric Company, Schenectady, NY (US)

(*) Notice: Subject to any disclaimer, the term of this patent is extended or adjusted under 35 U.S.C. 154(b) by 575 days.

(21) Appl. No.: 11/240,886

(22) Filed: Sep. 30, 2005

(65) Prior Publication Data

US 2007/0074727 A1   Apr. 5, 2007

(51) Int. Cl.
| | |
|---|---|
| A62B 7/10 | (2006.01) |
| A62B 7/00 | (2006.01) |
| A61M 15/00 | (2006.01) |
| A61M 16/00 | (2006.01) |
| B01D 59/26 | (2006.01) |
| B01D 53/02 | (2006.01) |

(52) U.S. Cl. ............... 128/205.28; 128/205.27; 128/205.29; 128/205.23; 128/205.12; 128/202.26; 128/204.18; 95/139; 96/117.5

(58) Field of Classification Search .......................... 128/205.27–205.29, 205.23, 205.12, 202.26, 128/204.18; 96/117.5, 117, 115, 116, 147; 95/139; 422/83, 85, 86, 88, 122; 210/193, 210/504, 506

See application file for complete search history.

(56) References Cited

U.S. PATENT DOCUMENTS

| | | | |
|---|---|---|---|
| 2,815,662 A | 12/1957 | Thomas | |
| 2,918,356 A | 12/1959 | Hay | |
| 3,088,810 A | 5/1963 | Hay | |
| 3,548,639 A | 12/1970 | Krause | |
| 3,615,233 A * | 10/1971 | Doering et al. | 422/117 |
| 4,150,570 A | 4/1979 | Fuller | |
| 5,224,373 A | 7/1993 | Williams et al. | |
| 5,360,002 A | 11/1994 | Smith | |
| 5,432,094 A * | 7/1995 | Delente | 436/127 |
| 5,440,927 A | 8/1995 | Chu et al. | |
| 5,558,088 A * | 9/1996 | Smith | 128/205.28 |
| 5,766,312 A | 6/1998 | Furhmann et al. | |
| 5,834,626 A * | 11/1998 | De Castro et al. | 73/23.3 |
| 5,879,943 A | 3/1999 | Ando et al. | |
| 6,043,096 A | 3/2000 | Evtodienko et al. | |
| 6,131,571 A * | 10/2000 | Lampotang et al. | 128/204.21 |
| 6,216,690 B1 | 4/2001 | Keitel et al. | |
| 2003/0121418 A1 * | 7/2003 | Loop et al. | 96/117.5 |

* cited by examiner

OTHER PUBLICATIONS

Degradation of Inhalation Anaesthetics by CO2 Absorbers—3 RC 1, Peter F. Conzen, Anaesthesia and Intesive Care Medicine, Ludwig-Maximilians-Univeresity Klinikum Großhadem, Munich, Germany, May 29, 1999, www.euroanesthesia.org/education/rc_amsterdam/03rcl.HTM.

*Primary Examiner*—Patricia M Bianco
*Assistant Examiner*—Nihir Patel
(74) *Attorney, Agent, or Firm*—Andrus, Sceales, Starke & Sawall, LLP

(57) ABSTRACT

An improved carbon dioxide absorber for use in a closed circuit patient breathing system has a canister insertable in the breathing circuit for receiving recirculating breathing gases. The canister contains a pelletized $CO_2$ absorbent material that removes the $CO_2$ from the breathing gases passing through the absorber. A quantity of the $CO_2$ absorbent material is treated with a chemical indicator such that the chemical indicator makes a color change indicative of the state of the absorptive capacity of the absorbent material. A separate quantity of the $CO_2$ absorbent material is treated with a second chemical indicator. The second chemical indicator changes color to indicate the degree of dryness of the $CO_2$ absorbent material. The second chemical indicator may comprise cobalt chloride and serves to indicate the potential for excessive heat generation and toxic gas generation conditions within the $CO_2$ absorbent canister.

15 Claims, 2 Drawing Sheets

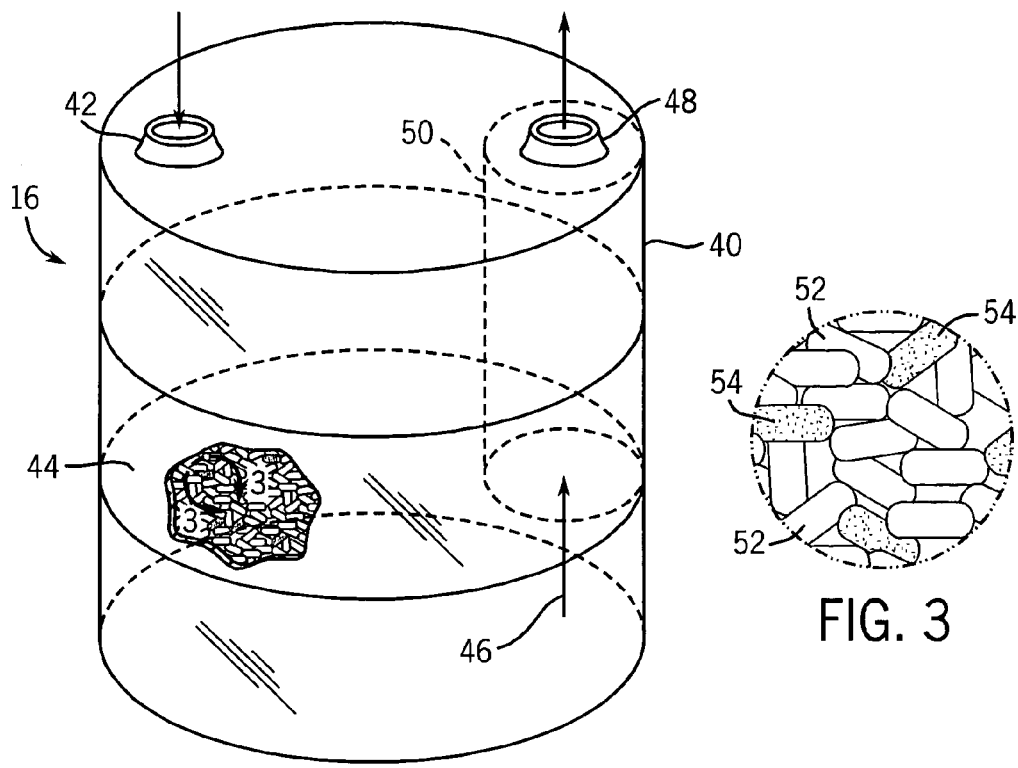
FIG. 2
FIG. 3
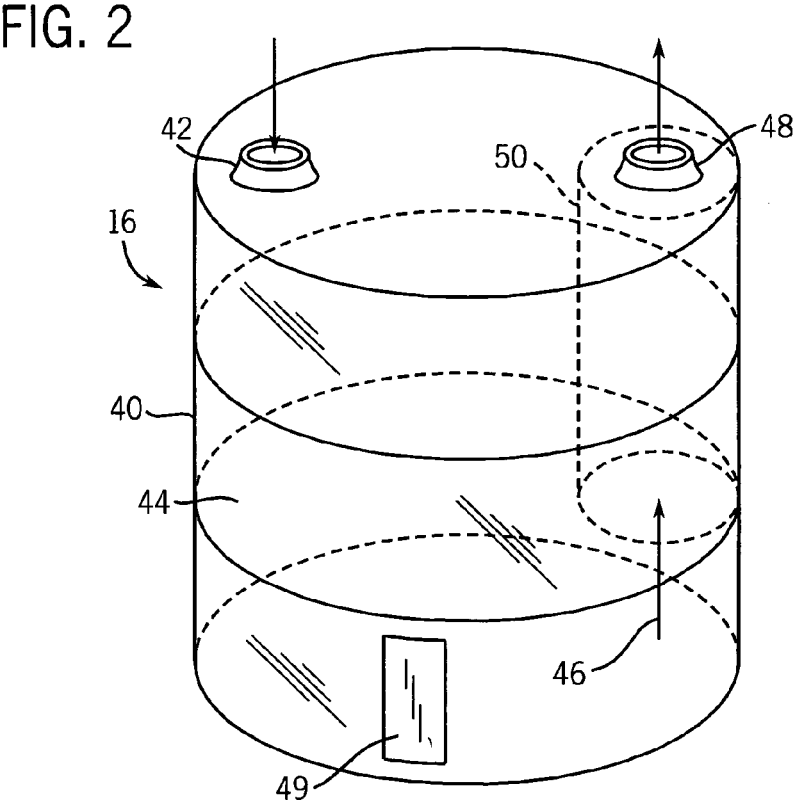
FIG. 4

SAFETY DEVICE FOR BREATHING CIRCUIT CARBON DIOXIDE ABSORBER

FIELD OF THE INVENTION

The present invention relates to an improved carbon dioxide absorber canister for use in patient anesthesia delivery machines and having an indicator for the presence of a hazardous condition within the absorber. The hazardous condition may be the presence of elevated temperatures or one that generates toxic gases within the absorber.

BACKGROUND AND SUMMARY

Anesthesia delivery machines provide breathing gases, such as air, oxygen, helium, and nitric oxide, along with anesthetic agents to a patient during surgery or diagnostic procedures. A recirculating breathing circuit returns expired breathing gases back to the patient. A recirculating breathing circuit conserves anesthetic agent and lowers the overall cost of a medical procedure. The use of a recirculating breathing circuit also provides the additional advantage of conserving heat and moisture in the breathing gases, thereby avoiding discomfort to the patient.

One problem that must be overcome in a recirculating breathing circuit is the removal of carbon dioxide ($CO_2$), a byproduct of cellular metabolism, from the expired breathing gases before they can be delivered back to the patient. This is performed by a $CO_2$ absorber canister in the breathing circuit. The canister is filled with a $CO_2$ absorbent material that removes the $CO_2$ from the expired gases as they pass through the canister. Two common types of $CO_2$ absorbent materials are soda lime and baralyme although there are other chemicals that may serve this purpose. The $CO_2$ absorbent materials may include a color changing indicator that informs a clinician when the $CO_2$ absorbing reagents have been used up and the $CO_2$ absorbent material must be replaced. U.S. Pat. No. 3,088,810 to Hay discloses a transparent $CO_2$ absorber canister utilizing a $CO_2$ absorbent material that is treated with an indicator agent that, during the course of $CO_2$ absorption, indicates the depletion of the absorptive capacity of the material by gradually changing color. Ethyl violet is disclosed as being one such indicator which changes color from white to blue/purple as the absorptive capacity of the absorbent becomes exhausted. U.S. Pat. No. 5,360,002 to Smith discloses a similar $CO_2$ absorbent material in a disposable canister.

The $CO_2$ absorbent material found in the canister of a recirculating breathing system typically contains about 20% water by weight. This hydration helps to initiate the reaction that removes the $CO_2$ gas from expired breathing gases passing through the canister. However, as noted below, the potential exists in a $CO_2$ absorber canister for the $CO_2$ absorbent material to dry out before the $CO_2$ reagents have been expended. The water content of a $CO_2$ absorbent material considered to be "dried out" varies among $CO_2$ absorbent materials. While soda lime is considered to be dried out at a water concentration less than approximately 2% water by weight, baralyme is considered to be dried out at concentrations less than approximately 5% water by weight. At these water concentrations, the $CO_2$ absorbent reaction is still maintained.

However, the anesthetic agent in the expired breathing gases will react with the dried out $CO_2$ absorbent material in an exothermic reaction which produces excess heat and toxic substances within the breathing circuit. The type of reaction that takes place in the absorber canister, as well as the products of the anesthetic agent/dried out $CO_2$ absorbent material reaction, is dependent on the type of anesthetic agent in use. Anesthetic agents such as desflurane, enflurane, and isoflurane react with dried $CO_2$ absorbent material to produce carbon monoxide. Carbon monoxide is dangerous because of the toxic effects it has on the body, a danger that is exacerbated with sick or surgical patients. Other anesthetic agents react with dried $CO_2$ absorbent material to form other toxic compounds. Halothane reacts with $CO_2$ absorbent material to form a substance called BCDFE (2-bromo-2-chloro-1,1-difluoroethylene) while, in the case of sevoflurane, a known nephrotoxin referred to as Compound A (fluoromethyl-2,2-difluoro-1-(trifluoromethyl)vinyl ether) is formed. Additionally, the chemical reaction that produces Compound A is highly exothermic and the increased heat speeds up the reaction, thus creating more Compound A and a potential fire hazard.

While the potential for the existence of these adverse circumstances has always been present in recirculating breathing systems, these reactions only truly began to pose a potential threat to patients with the recent increased focus on and use of low-flow and minimal-flow anesthesia techniques. Due to economical constraints, newer low-flow and minimal-flow anesthesia systems are designed to have more efficient breathing circuits that recycle as much medical gas as possible and use lower flow rates of breathing gas, thus using less anesthetic agent and medical gas and reducing the overall cost of anesthetization, as is taught by Keitel et. al. in U.S. Pat. No. 6,216,690. The increased recirculation of the breathing gases and the lower gas flow rates result in greater overall concentrations of toxic gases produced as byproducts of undesired reactions within the patient breathing circuit that were not seen before in less efficient systems.

The $CO_2$ absorbent material in the canister may become dried out, thus producing toxic byproducts, in a variety of ways. The largest contributor is the breathing gases themselves. Breathing gases are supplied from tanks or manifolds in which the gas is compressed. During compression of the gases, water from the gases is removed and, as such, they are extremely dry when the pressure is lowered and the gases are supplied to the patient. While breathing gases expired by the patient have a humidity near 100%, standard ventilation procedures utilize a small, continuous flow of breathing gas through the breathing circuit, known as a bias flow. This bias flow reduces the patient's airway resistance, reducing the effort required to carry out respiration as well as increasing the overall efficiency of the mechanical ventilation that accompanies anesthesia. This bias flow will constantly place a quantity of dry medical gas in contact with the $CO_2$ absorbent material, thus promoting drying out the $CO_2$ absorbent material, notwithstanding the humidity of the breathing gases expired by the patient. This drying out is increased during periods of high gas flow, such as the inductance and emergence phases of anesthesia, when the bias flow is supplemented with increased amounts of fresh gas.

$CO_2$ absorbent material may also become dried out as a result of nonstandardized hospital procedure in shutting down and starting up anesthetic delivery apparatus. This can result in failure to completely close the valves on the medical gas supply tanks or manifolds. This may result in a small flow of dried medical gas coming in contact with the $CO_2$ absorbent material over an extended period of time, such as the course of a night or weekend. The existence of this problem is supported by medical data showing that patient exposure to toxic substances formed because of dried $CO_2$ absorbent material are most likely to occur during the first procedure performed at the start of the week.

The final factor contributing to this problem is the common hospital practice of reusing $CO_2$ absorbent material until its $CO_2$ absorbent properties have been spent. This prolongs the time in which a $CO_2$ absorbent material may be exposed to medical gases in a sufficient quantity to dry the $CO_2$ absorbent material, thus creating the aforementioned hazardous conditions.

It would, therefore, be desirable to provide a breathing circuit $CO_2$ absorber canister with means to indicate the potential for hazardous conditions, such as the generation of heat and/or toxic gases. Preferably such an indicator should be provided in a manner that avoids interference with the action of the $CO_2$ absorbent depletion indicator.

Color changing moisture indicators utilizing cobalt chloride ($CoCl_2$) have been in use for some time and are well known. U.S. Pat. No. 5,224,373 to Williams discloses a container with a flexible humidity indicator using such a chemical and capable of displaying information about the humidity of the environment inside the container. U.S. Pat. No. 4,150,570 to Fuller shows a humidity sensing device for visually indicating changes in relative humidity as by numbers or text.

However, such prior art does not specifically address the problem of monitoring hazardous heat and toxic gas generating conditions within a recirculating breathing system $CO_2$ absorber canister.

SUMMARY OF THE INVENTION

The present invention is thus directed to an improved carbon dioxide absorber for use in a closed circuit patient breathing system. The absorber comprises a canister that is insertable in the breathing circuit for receiving the recirculating breathing gases. The canister contains a $CO_2$ absorbent material that removes the $CO_2$ from the breathing gases passing through the absorber. The $CO_2$ absorbent material may be in granule or pellet form. A quantity of the $CO_2$ absorbent material is treated with a chemical indicator that makes a color change indicative of the remaining absorptive capacity of the absorbent material. A separate, preferably smaller, quantity of the $CO_2$ absorbent material is treated with a second chemical indicator such that the second chemical indicator changes color indicative of the dryness of the $CO_2$ absorbent material. The second chemical indicator may comprise cobalt chloride.

During clinical use, resulting in exposure to dry medical gases, the $CO_2$ absorbent material in the $CO_2$ absorber loses moisture. As the absorbent material dries out, the cobalt chloride indicator turns from a pink-brown color to blue, thus indicating the potential for hazardous heat and toxic gas generating conditions within the $CO_2$ absorbent canister.

Additionally, and regardless of the dryness of the $CO_2$ absorbent material, the cobalt chloride indicator will also indicate of the existence of a high temperature in the canister by making a color change from pink to blue. The clinician is thus also warned of the existence of this hazardous condition.

Other advantages of the breathing circuit $CO_2$ absorber with a hazardous condition safety device will be apparent from the following detailed description and accompanying drawings.

BRIEF DESCRIPTION OF THE DRAWINGS

In the drawings:

FIG. 2 is a view of the $CO_2$ absorber of the present invention.

FIG. 3 is a detailed view of a portion of the showing of FIG. 2.

FIG. 4 shows a modification of the $CO_2$ absorber show in FIG. 2.

DETAILED DESCRIPTION

Figure 1:
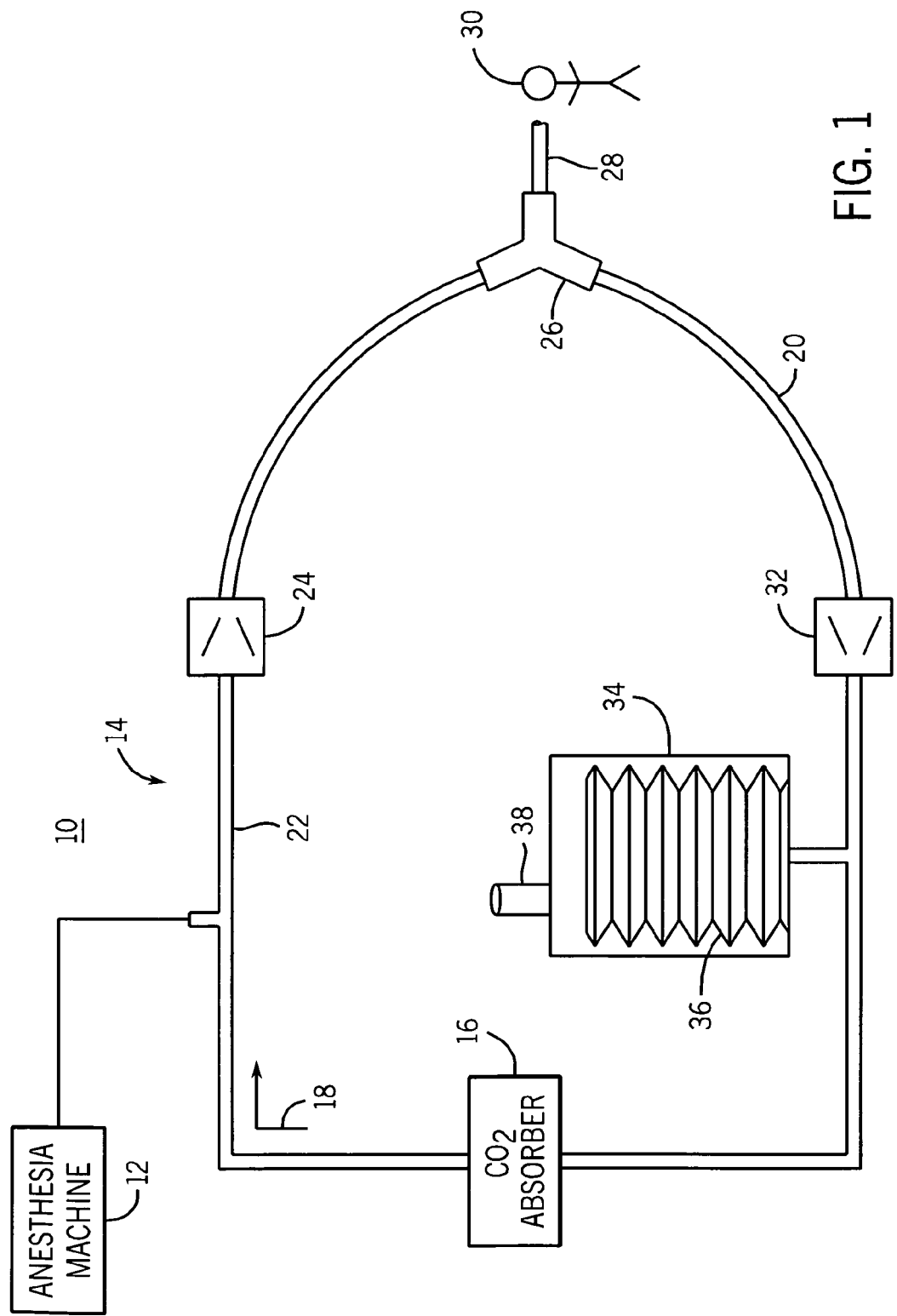
FIG. 1 is a schematic diagram of a breathing circuit for an anesthesia machine in which the $CO_2$ absorber of the present invention may be used.

FIG. 1 shows an apparatus 10 for administering anesthesia to a patient 30 having an anesthesia machine 12 and a breathing circuit 14. Breathing circuit 14 includes a $CO_2$ absorber 16 through which recirculating breathing gases flow in the direction of arrow 18 from expiration limb 20 to inspiration limb 22. In the inspiration limb 22, fresh breathing gases and anesthetic agent from the anesthesia machine 12 join the breathing gases already present in the breathing circuit 14. The breathing gases flow through inspiration check valve 24 in inspiration limb 22 to Y-connector 26 connected to patient limb 28 that delivers gases to patient 30. Upon expiration, the exhaled gases flow back through the patient limb 28 into Y-connector 26, into expiration limb 20, and through an expiration check valve 32. The exhaled gases flow into assembly 34 having a bellows 36 that expands to receive the exhaled gases. Bellows 36 collapses to provide a positive pressure that drives the breathing gases through the breathing circuit 14 responsive to a bellows driver connected to conduit 38 that pressurizes assembly 34. When bellows 36 collapses, the breathing gases flow from the bellows into $CO_2$ absorber 16 in which the $CO_2$ in the expired breathing gases is removed to supply $CO_2$-free gas to inspiration limb 22.

FIG. 2 shows a $CO_2$ absorber 16 constructed in accordance with the present invention. $CO_2$ absorber 16 includes canister 40 having canister inlet port 42 for receiving breathing gases from bellows 36. Inside canister 40 is a $CO_2$ absorbent material 44 through which the breathing gases pass for removal of $CO_2$. The $CO_2$ absorbent material may be soda lime (a mixture of hydrated lime ($Ca(OH)_2$) and sodium hydroxide ($Na(OH)$), but alternative $CO_2$ absorbent materials such as baralyme may be used. Such material 44 is usually in granular or pellet form. A baffle 50 or other means may be provided in canister 40 to ensure proper exposure of the breathing gases to $CO_2$ absorbent material 44 and so that the gases follow a flow path 46 up through a canister outlet port 48 and into the expiration limb 22. In the embodiment shown in FIG. 2, canister 40 is preferably formed of a transparent or translucent material to permit viewing of the contents of the canister. In the embodiment shown in FIG. 4, canister 40 may be formed of an opaque material having a viewing window 49.

$CO_2$ absorbent material 44 may be treated with a chemical indicator, such as ethyl violet, that changes color from white to blue/violet as the $CO_2$ absorptive capacity of the absorbent material becomes exhausted. For this purpose, the chemical indicator may be admixed with the absorbent material of the pellets, the pellets may be coated with the chemical indicator, or the chemical indicator may be combined with the absorbent material in some other appropriate manner.

To provide the toxic gas and high temperature warning features, the present invention utilizes a mixture of $CO_2$ absorbent material pellets. A majority of the pellets, shown as 52 in the detailed drawing of FIG. 3, are treated with the absorptive capacity chemical indicator. A smaller portion of the pellets, shown as 54 in the detailed drawing of FIG. 3, form sentinel pellets that are not treated with the absorptive capacity indicator, but rather are treated with cobalt chloride to indicate the dryness and/or temperature of $CO_2$ absorbent material 44. This small fraction of cobalt chloride treated sentinel pellets 54 may be on the order of 10% of the total mixture of $CO_2$ absorbent pellets 44. As the $CO_2$ absorbent material 44 dries, the appearance of sentinel pellets 54 changes from pink to blue.

This mixture of absorptive capacity indicator pellets 52 and hazardous condition indicator pellets 54 provides sufficient contrast for a clinician to observe both indicator color changes independently and be able to distinguish between absorptive capacity depletion and dryness/high temperature hazardous conditions in $CO_2$ absorber 16. A mixture of $CO_2$ absorbent pellets that is predominantly comprised of absorptive capacity indicator pellet 52 with a small fraction of indicator pellets 54 also presents the advantage of predominantly showing the indication of absorptive capacity, the more commonly needed indication by the clinician. However, in the less frequent instances when the $CO_2$ absorbent material may become dried out, there is a sufficient concentration of indicator sentinel pellets 54 for the clinician to become aware of this condition as well. Cobalt chloride in its hydrated form has a pink appearance to an observer.

The cobalt chloride indicator treated sentinel pellets 54 also provide an indication of a high temperature condition existing within $CO_2$ absorber canister 16. This feature utilizes a property of cobalt chloride that is not generally used for indicative purposes. When the temperature surrounding cobalt chloride exceeds 110° Centigrade (230° Fahrenheit), the hydrated form of the cobalt chloride spontaneously releases all of its bound water molecules. This changes the appearance of the cobalt chloride from the hydrated pink color to the dehydrated blue color. In $CO_2$ absorbent canisters, where adverse chemical reactions between anesthetic agents and the absorbent material may create high temperatures and potential fire and/or explosion hazards, this additional property of cobalt chloride treated sentinel pellets 54 can serve as an immediate warning of this hazardous condition within the $CO_2$ absorber canister.

In summary, when the clinician observes the $CO_2$ absorbent material within the $CO_2$ absorber canister under proper and safe operating conditions, the $CO_2$ absorbent material will appear predominantly white (from the absorptive capacity chemical indicator pellets 52) with a mixture of pink sentinel pellets 54. However, as the $CO_2$ absorbent material drops in quality either due to the expiration of the absorptive capacity, dehydration of the absorbent material, or increased temperatures within the canister, either or both of the previously white $CO_2$ absorbent material pellets 52 or the previously pink $CO_2$ absorbent material pellets 54 will darken to a blue hue. Therefore, the clinician need only look for the presence of a darker cast to the $CO_2$ absorbent material to be warned that corrective action must be taken. As noted above, closer examination will enable the clinician to discern the exact nature of the adverse condition in $CO_2$ absorber canister 16.

Various alternatives and embodiments are contemplated as being within the scope of the following claims, particularly pointing out and distinctly claiming the subject matter regarded as the invention.

What is claimed is:

1. An improved $CO_2$ absorber for a patient breathing circuit capable of indicating the potential for, or existence of, hazardous conditions in the $CO_2$ absorber, the breathing circuit recirculating $CO_2$ laden breathing gases which may also contain an anesthetic agent, said absorber comprising:

a canister suitable for insertion in the breathing circuit so that the recirculating breathing gases pass through the canister, the canister being formed to permit viewing of contents of the canister;

a pelletized $CO_2$ absorbent material in said canister for removing $CO_2$ from breathing gases, said absorbent material being susceptible to drying by the breathing gases in the breathing circuit, at least a portion of the pellets of absorbent material having an indicator changing color from a first color to a second color as the absorptive capacity of the $CO_2$ absorbent material becomes exhausted; and a plurality of sentinel pellets of $CO_2$ absorbent material disposed throughout the pelletized $CO_2$ absorbent material, said sentinel pellets containing a cobalt chloride substance and changing from a third color to the second color to indicate the dehydration of the $CO_2$ absorbent material of the sentinel pellets;

wherein the first color and the third color are different colors.

2. An improved $CO_2$ absorber according to claim 1 wherein substantially more of said pelletized $CO_2$ absorbent material is present in the $CO_2$ absorber canister than sentinel pellets.

3. An improved $CO_2$ absorber according to claim 2 wherein said sentinel pellets comprise 10% of the $CO_2$ absorbent material in the said canister.

4. An improved $CO_2$ absorber according to claim 1 wherein the change of color of the sentinel pellets from the third color to the second color indicates the generation of a toxic gas by the $CO_2$ absorbent material.

5. An improved $CO_2$ absorber according to claim 4 wherein said anesthetic agent comprises desflurane, enflurane, and isoflurane, and said toxic gas is carbon monoxide (CO).

6. An improved $CO_2$ absorber according to claim 4 wherein said anesthetic agent is halothane and wherein said toxic gas is BCDFE (2-bromo-2-chloro-1,1-difluoroethylene).

7. An improved $CO_2$ absorber according to claim 4 wherein said anesthetic agent is sevoflurane wherein said toxic gas is compound A (fluoromethyl-2,2-difluoro-1-(trifluoromethyl) vinyl ether).

8. An improved $CO_2$ absorber according to claim 1 wherein said absorber is further defined as the change of color of the sentinel pellets from the third color to the second color indicates a hazardous condition comprising an elevated temperature within the absorber.

9. An improved $CO_2$ absorber according to claim 8 wherein said elevated temperature is a temperature in excess of 110° Centigrade (230° Fahrenheit).

10. An improved $CO_2$ absorber according to claim 1 wherein said $CO_2$ absorbent material further comprises soda lime or baralyme.

11. An improved $CO_2$ absorber of claim 1, wherein the cobalt chloride substance changes from the third color to the second color to indicate that the absorbent material has exceeded a threshold temperature.

12. A $CO_2$ absorber for a patient breathing circuit that indicates the existence of a hazardous condition within the $CO_2$ absorber, the patient breathing circuit recirculating $CO_2$ laden breathing gases containing an anesthetic agent to the $CO_2$ absorber, the $CO_2$ absorber comprising:

a canister suitable for insertion in the breathing circuit so that the recirculating breathing gases pass through the canister, the canister being formed to permit viewing of contents of the canister;

a pelletized $CO_2$ absorbent material in the canister that removes $CO_2$ from the breathing gases, the $CO_2$ absorbent material being susceptible to drying by the breathing gases in the breathing circuit, at least a portion of the pelletized $CO_2$ absorbent material having an indicator that changes color as the absorptive capacity of the material becomes exhausted; and a plurality of sentinel pellets of $CO_2$ absorbent material disposed throughout the pelletized $CO_2$ absorbent material, the sentinel pellets containing a cobalt chloride substance that changes from a first color to a second color to indicate the hydration level of the sentinel pellets.

13. The $CO_2$ absorber of claim 12, wherein the cobalt chloride substance changes from the first color to the second color to indicate that the absorbent material has exceeded a threshold temperature.

14. The $CO_2$ absorber of claim 13, wherein the threshold temperature is 110° centigrade.

15. The $CO_2$ absorber of claim 12 wherein the cobalt chloride substance changes from the first color to the second color to indicate that the sentinel pellets have become dehydrated.

* * * * *